United States Patent [19]

Blumberg et al.

[11] Patent Number: 6,036,747
[45] Date of Patent: Mar. 14, 2000

[54] COLUMN SPECIFIC PARAMETERS FOR RETENTION TIME LOCKING IN CHROMATOGRAPHY

[75] Inventors: Leonid M. Blumberg, Hockessin, Del.; Alan D. Broske, West Chester, Pa.

[73] Assignee: Hewlett-Packard Company, Palo Alto, Calif.

[21] Appl. No.: 09/122,273

[22] Filed: Jul. 24, 1998

[51] Int. Cl.[7] .................................................. B01D 15/08
[52] U.S. Cl. ................................................ 95/82; 96/102
[58] Field of Search ..................... 95/82–89; 96/101–107

[56] References Cited

U.S. PATENT DOCUMENTS

| | | | |
|---|---|---|---|
| 4,824,446 | 4/1989 | Mowery, Jr. ............................. | 55/386 X |
| 4,927,532 | 5/1990 | Pospisil et al. ......................... | 55/386 X |
| 4,948,389 | 8/1990 | Klein et al. .............................. | 95/87 X |
| 4,994,096 | 2/1991 | Klein et al. .............................. | 95/82 X |
| 5,108,466 | 4/1992 | Klein et al. .............................. | 95/82 X |
| 5,281,256 | 1/1994 | Sacks et al. .............................. | 95/86 |
| 5,405,432 | 4/1995 | Snyder et al. ............................ | 95/82 |
| 5,436,166 | 7/1995 | Ito et al. .................................. | 436/161 |
| 5,545,252 | 8/1996 | Hinshaw et al. ....................... | 96/102 X |
| 5,670,379 | 9/1997 | Ito et al. .................................. | 436/161 |
| 5,738,707 | 4/1998 | Colombo et al. ...................... | 96/102 X |
| 5,892,458 | 4/1999 | Anderer et al. ......................... | 95/82 X |

FOREIGN PATENT DOCUMENTS

| | | | |
|---|---|---|---|
| 1-191055 | 8/1990 | Japan .................................... | 73/23.23 |

OTHER PUBLICATIONS

"Standard Test Method For Detailed Analysis Of Petroleum Naphthas Through n–Nonane By Capillary Gas Chromatography", ASTM Committee D–2 on Petroleum Products and Lubricants, Published Oct. 1992 (Originally published as D 5134–90.

Hewlett–Packard Co., Operation Manual, "5880A Gas Chromatograph PNA Analyzer, Option 850", Oct. 1982, Revised Jul. 1983; Part No. 18900–90850.

Hewlett–Packard Co., Operation Manual, "The HP 5880A Gas Chromatograph and the HP85 Computer Configured for PNA Analysis"; 18900–90603; Mar. 1985 Rev. B, Apr. 1986 Rev C.

Hewlett–Packard Instruction Manual, "GC–AED Quick-Screen Methods", Sep. 20, 1994, 51 pages.

"HP 5898A Microbial Identification System" Operating Manual, Version 3.0 Part No. 19298–90100, Mar., 1984 (Rev. Oct. 1987).

*Primary Examiner*—Robert Spitzer

[57] ABSTRACT

The present invention provides an improved method for calculating and adjusting the column head pressure of a GC instrument based on the column's plate capacity, $N_c$, and film thickness, $d_s$, measured ideally during the manufacturing process and identified with the column such that software associated with the GC instrument can calculate a new column head pressure based on the relationship between the plate capacity and film thickness of the existing column to the plate capacity and film thickness of the new or shortened column. The column head pressure of the GC is adjusted to the new column head pressure to provide a reduction in the column-to-column non-reproducibility error in retention times of all peaks.

28 Claims, 9 Drawing Sheets

COLUMN SPECIFIC PARAMETERS FOR RETENTION TIME LOCKING IN CHROMATOGRAPHY

The present invention relates to methods for gas chromatography and, more particularly, to column specific parameters (plate capacity and film thickness) that provide for the reduction of unpredictable errors of retention times of analytes eluting from different columns having the same stationary phase type, but with different column dimensions (including different film thickness), different carrier gases and/or different detectors requiring different outlet pressures.

BACKGROUND OF THE INVENTION

Chromatographers spend a significant portion of their time developing and optimizing chromatographic methods for the separation, identification, and quantification of specific compounds within a sample. Such a chromatographic method will specify the use of a column having defined column parameters (e.g., length, stationary phase, and internal diameter) as well as operating parameters for the gas chromatograph ("GC"). The operating parameters include carrier gas type and pressure, oven temperature, and temperature ramp rates. One problem facing all chromatographers is the inability to exactly replicate column and operating parameters in accordance with a prescribed or translated chromatographic method such that chromatographic retention times are reproducible from one GC to another. Additionally, there exists an ongoing need for column trimming as normal operation results in deposits of non-volatile compounds at the head of the column, resulting in contamination that causes retention time shifts and the distortion of peak shapes. This contamination necessitates the removal of a portion of the column (resulting in a shortened column) such that retention times using the original operating parameters are shorter.

A typical GC 10 is illustrated in FIG. 1 and includes a column 18 positioned within an oven 24. Chromatographic separation of a sample 20 is accomplished by injecting the sample 20 into a pressurized carrier gas through an injection port 12 into the column 18. Either manual control of pressure valve 14 or electronic pneumatic control via control signal 15 and controller interface 16 provides for adjusting the pressure of the carrier gas at the head of the column 18 (hereinafter "column head pressure") in response to a control signal. A heating unit 26 provides heat to the oven 24 in response to internal control signals. The carrier gas/sample combination passing through column 18 is exposed to a temperature profile resulting from the operation of the heater 26 within oven 24. Internal sensor 28 allows for computer monitoring of conditions within oven 24. Mass flow controller 22 ensures GC 10 is sufficiently vented. There is a direct correlation between the temperature profile and the retention time of different compounds making up the sample in the column. As compounds elute from the column 18, a detector 30 generates an electrical signal corresponding to some characteristic of the compounds. FIG. 2 illustrates the electronics employed for controlling the GC, including keypad 38, computer 40 and controller 42. Computer 40 includes a central processing unit, memory 41 and associated devices, such as random access memories, read-only memories, input/output isolation devices, and other components.

Locking the retention times of the new column to match the retention times of the original column without numerous recalibrations has been shown to provide an improvement in one or more of the following: substitution of any available column having the same stationary phase coating as the original column; reoptimization and direct comparability to existing chromatographic methods; a predictable improvement in analysis speed; improved troubleshooting and diagnostics; increased remote supportability, improved accuracy of quantification or resolution; and the identification of compounds.

There exists a need for measuring and supplying column specific parameters that identify inherent characteristics of the column such that upon the replacement or modification of a column, a corrected head pressure can be calculated that provides for retention time locking. Such parameters provide an improvement in the following areas: porting chromatographic methods between several instruments, saving time in method setup and validation; locking of retention times in a multiple of GC instruments using the same type of column, but different carrier gases and different detectors requiring different outlet pressures; and automated retention time locking where system software automatically calculates and adjusts the column head pressure of a GC.

It will be apparent from the foregoing that the column's stationary phase film thickness, $d_s$, and plate capacity, $N_c$, defined as $N_c = L/d_c$ where L is column length and $d_c$ is the internal diameter of the column, can be used as column specific parameters for improved retention time locking without lengthy calibration after the installation or routine maintenance of a column.

SUMMARY OF THE INVENTION

The present invention provides an improved method for calculating and adjusting the column head pressure of a GC instrument such that the retention times of analytes eluting from a newly installed or shortened column on a GC instrument are matched to those of similar analytes eluting from other columns employing the same type of stationary phase, but where the columns have different dimensions (including different film thickness), different carrier gas types and possibly different outlet pressures (as required by different types of detectors). The new or modified column's film thickness, $d_s$, and plate capacity, $N_c$, defined $N_c = L/d_c$ where L is column length and $d_c$ is the internal diameter, are measured, ideally during the manufacturing process, and identified with the column such that when the column is installed in a GC instrument, the measured plate capacity and film thickness can also be provided to the GC instrument. Software associated with the GC instrument calculates a corrected column head pressure based on the relationship between the plate capacity and film thickness of the existing column, to the plate capacity and film thickness of the new or modified column. The column head pressure of the GC is adjusted to the corrected column head pressure to provide a reduction in the column-to-column non-reproducibility of retention times of all peaks and which is now generally described as retention time locking.

A user practicing an existing method with a column supplied with the plate capacity, $N_c$, and film thickness, $d_s$, parameters or some equivalents of these parameters, may quickly implement retention time locking. It would be advantageous for these parameters to be associated with every column, wherein, these parameters provide for the direct calculation of a new column head pressure that results in retention time locking.

DETAILED DESCRIPTION OF THE PREFERRED EMBODIMENTS

The present invention provides an improved method and apparatus for calculating and adjusting the column head pressure of a GC instrument by employing the plate capacity, $N_c$, of the column, and/or the stationary phase film thickness, $d_s$, of the column, which can be measured, ideally during the manufacturing process, and identified with the column for retention time locking by the GC instrument upon column installation.

Software associated with the GC instrument may calculate a new column head pressure based on the relationship between the plate capacity of an existing column, or nominal plate capacity specified in a chromatographic method, and the plate of a new or shortened column to be installed. Alternatively, or in combination with the correction made based on plate capacity, software associated with the GC instrument may calculate a new column head pressure based on the relationship between the film thickness of the existing column, or that specified in the chromatographic method, and the film thickness of the new or shortened column to be installed. The column head pressure of the GC instrument is adjusted to the new column head pressure to reduce the column-to-column non-reproducibility of retention time error of all peaks.

Plate capacity, $N_c$ may be employed for calculating a new column head pressure that compensates for variations in column length, column diameter, carrier gas type and outlet pressure. The retention times of analytes eluting from two different columns having the same film thickness, and the same temperature program may be locked by adjusting the column head pressure an amount corresponding to the respective plate capacity.

a. Measurement of Plate Capacity and Film Thickness

Figure 1:
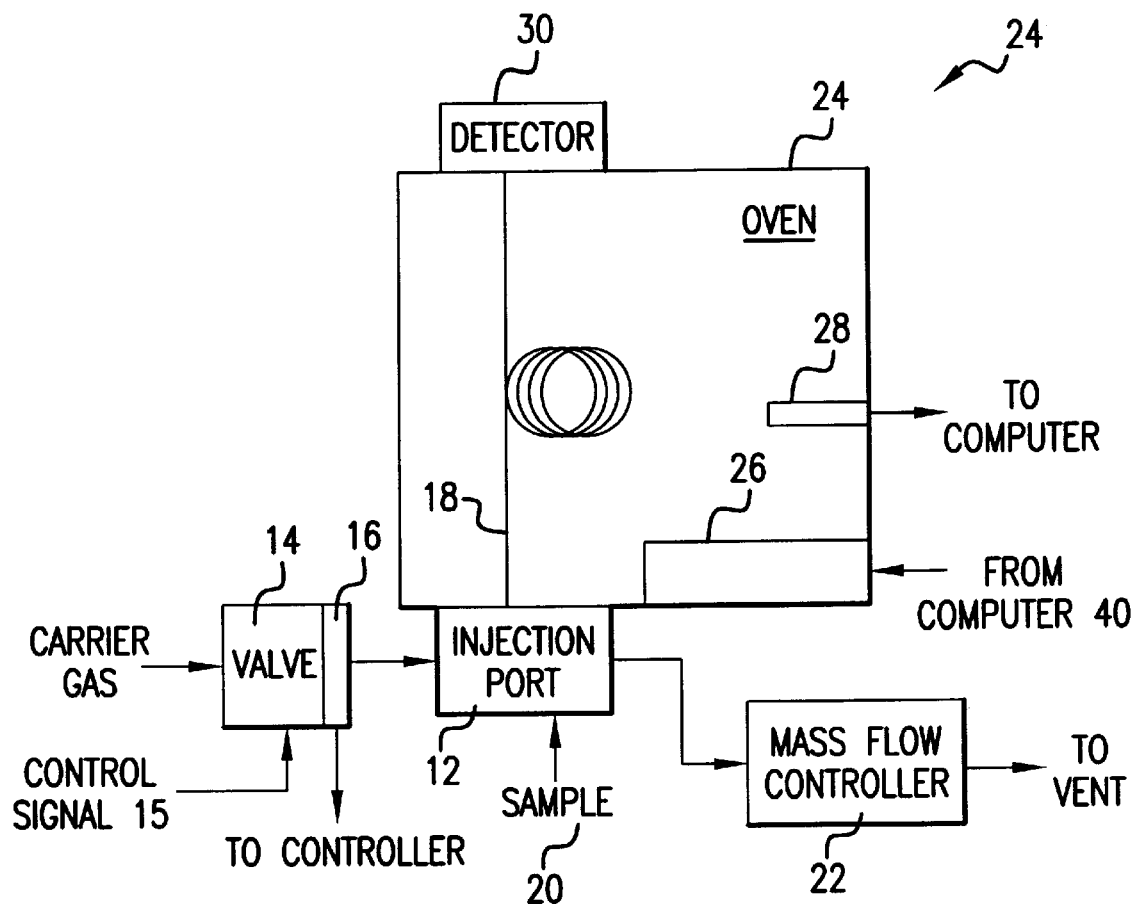
FIG. 1 illustrates a typical prior art GC instrument.
Figure 2:
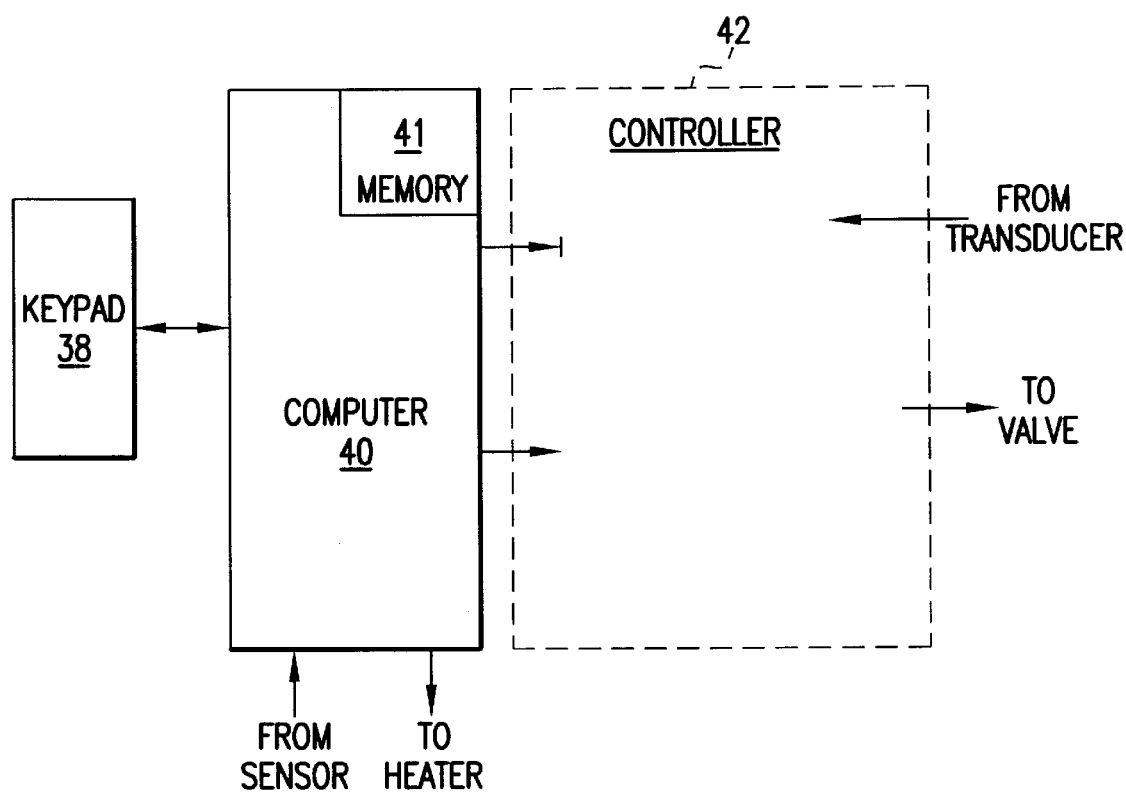
FIG. 2 illustrates the electronics and software associated with the prior art GC illustrated in FIG. 1.
Figure 3:
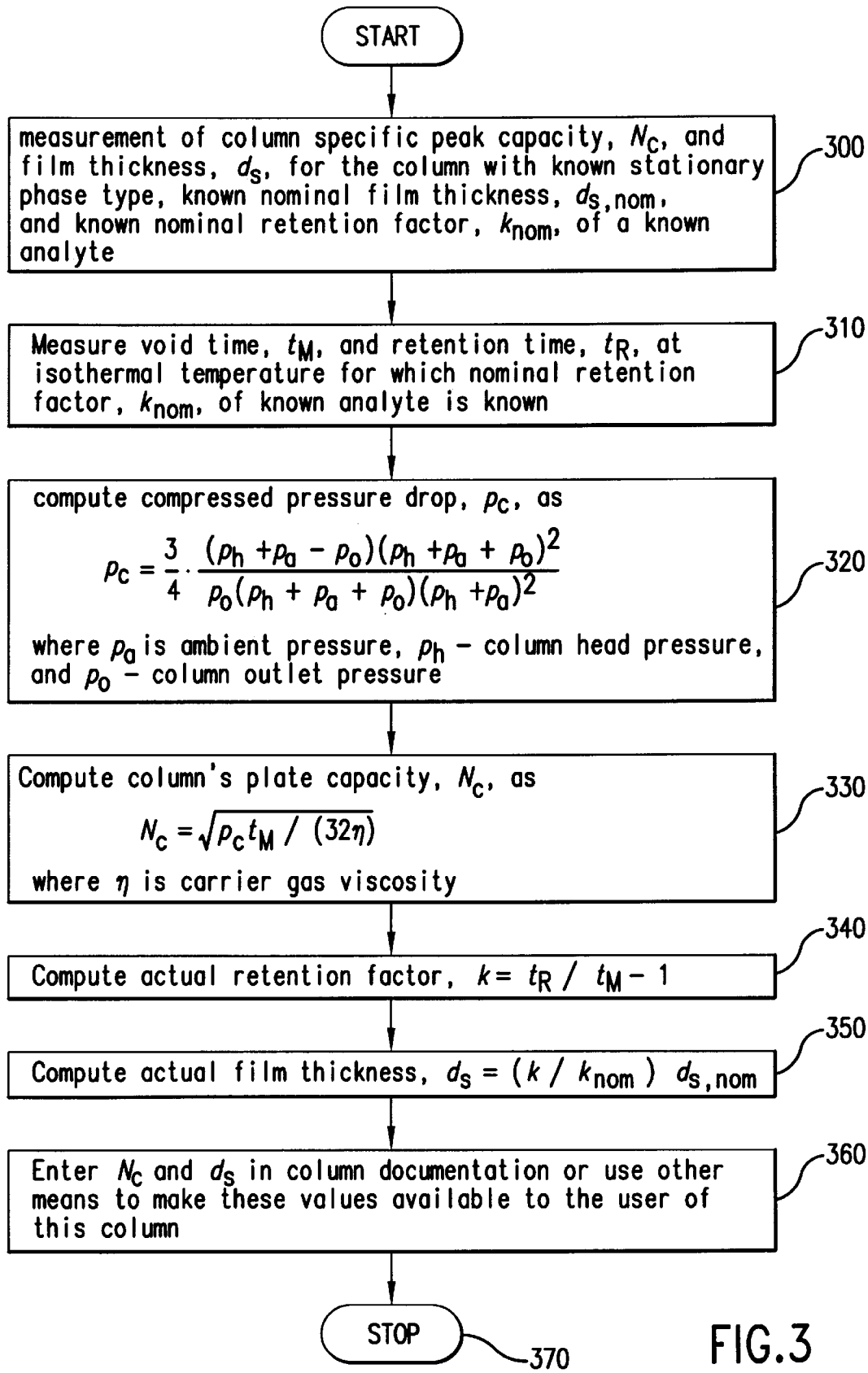
FIG. 3 illustrates method steps associated with the invention.

The invention, as illustrated in FIG. 3 provides for measurement and identification of the plate capacity, $N_c$, and/or the stationary phase thickness, $d_s$, for each column during the column manufacturing process. Step 300 recites the start of the measurement method. A column is installed in a gas chromatograph and a two-component mixture is analyzed under well controlled isothermal conditions. One component in the mixture is unretained while the other is retained. The unretained component is used for the measurement of void time, $t_M$ (step 310). The retention time, $t_R$, is employed for calculating the retention factor k and film thickness $d_s$. For better precision of measurement of $d_s$, the retention time, $t_R$, of the retained peak should be substantially larger than $t_M$.

To find the actual value of the plate capacity, $N_c$, the value of the compressed pressure drop, $p_c$, of the carrier gas passing through the column is used. Compressed pressure drop is defined as $p_c = r \cdot \bar{u}$ where $\bar{u}$ is average velocity of carrier gas and r is equal to the pneumatic resistance of the column. For a column with circular cross-section, $$r = \frac{32\eta L}{d_c^2}$$

where $d_c$=column internal diameter

L=column length $\eta$=carrier gas viscosity

For the purpose of calculation of plate capacity, $N_c$, from the measured data, compressed pressure drop, $p_c$, is calculated (step 320) as $$p_c = \frac{3}{4} \cdot \frac{(p_h + p_a - p_o)(p_h + p_a + p_o)^2}{p_o(p_h + p_a + p_o)(p_h + p_a)^2}$$

where $p_a$=ambient pressure $p_h$=column head pressure $p_o$=column outlet pressure Typically, $p_o$ is either vacuum or the same as $p_a$. However, for some detectors, such as AED (atomic emission detector), $p_o$ can be above $p_a$.

When $p_o$ is equal to $p_a$ (outlet pressure is the same as ambient pressure), the equation for $p_c$ becomes:

$$p_c = \frac{3}{4} \cdot \frac{p_h(2p_a + p_h)^2}{3p_a^2 + 3p_a p_h + p_h^2}$$

When $p_o$ is equal to 0 (vacuum at the outlet, typical for a GC/MS application), the equation for the compressed pressure drop, $p_c$, becomes:

$$p_c = \frac{3}{4}(p_h + p_a)$$

Once void time, $t_M$, has been measured, and $p_c$ has been calculated, $N_c$ can be calculated (step 330) from the equation:

$$N_c = \sqrt{\frac{p_c t_M}{32\eta}}$$

where $\eta$=viscosity of the carrier gas.

To find the actual value of the film thickness, $d_s$, for a column with known type of stationary phase, known nominal film thickness, $d_{s,nom}$, and known nominal retention factor value, $k_{nom}$, for a known analyte at known isothermal temperature, first time, $t_M$, of the known analyte can be measured. Then, actual retention factor, k, can be calculated (step 340) as $$k = t_R/t_M - 1.$$

Finally, actual film thickness, $d_s$, can be calculated (step 350) as $$d_s = (k/k_{nom}) \, d_{s,nom}.$$

The invention contemplates that a column manufacturer will measure and supply column specific parameters $N_c$ and $d_s$, or their equivalents with each column (step 360) to assist users in retention time locking. Step 370 indicates the completion of the measurement method.

b. Column Head Pressure Adjustment

The column head pressure required for retention time locking can be directly calculated and automatically or manually adjusted when column-specific values of $N_c$ and $d_s$ are measured and supplied with a column as previously set forth. $N_c$ and $d_s$ depend only on the column geometry and remain constant regardless of operational conditions, carrier gas type, oven temperature, and temperature program employed when practicing a specific method of chromatographic analysis. Where the plate capacity, $N_{c,new}$, and/or film thickness, $d_{s,new}$, of a new column are known, there are several direct and simplified methods for retention time locking, including the following:

1. Known Nominal Void Time and Nominal Film Thickness

Figure 4A:
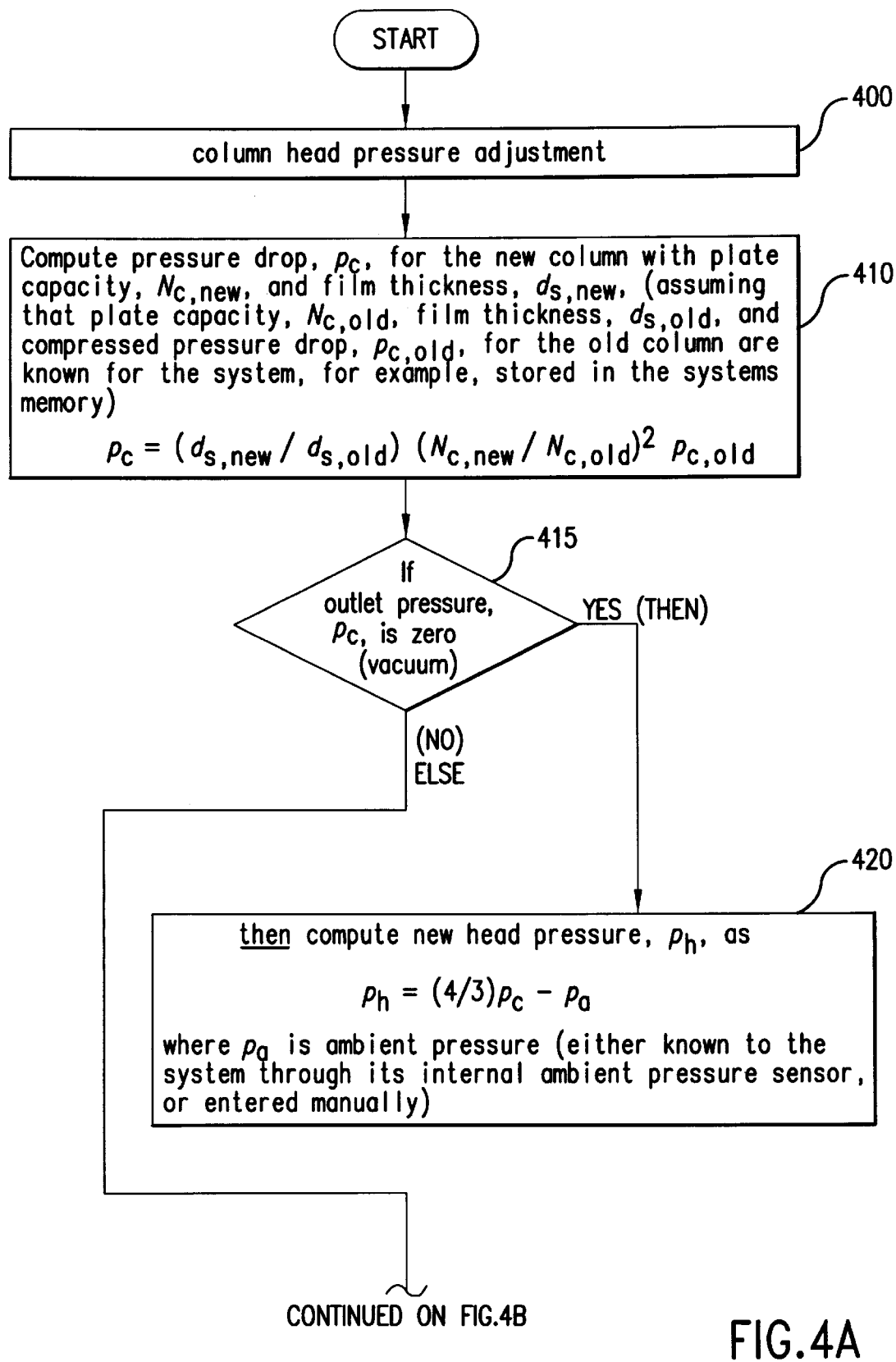
FIG. 4 illustrates method steps associated with the invention.
Figure 4B:
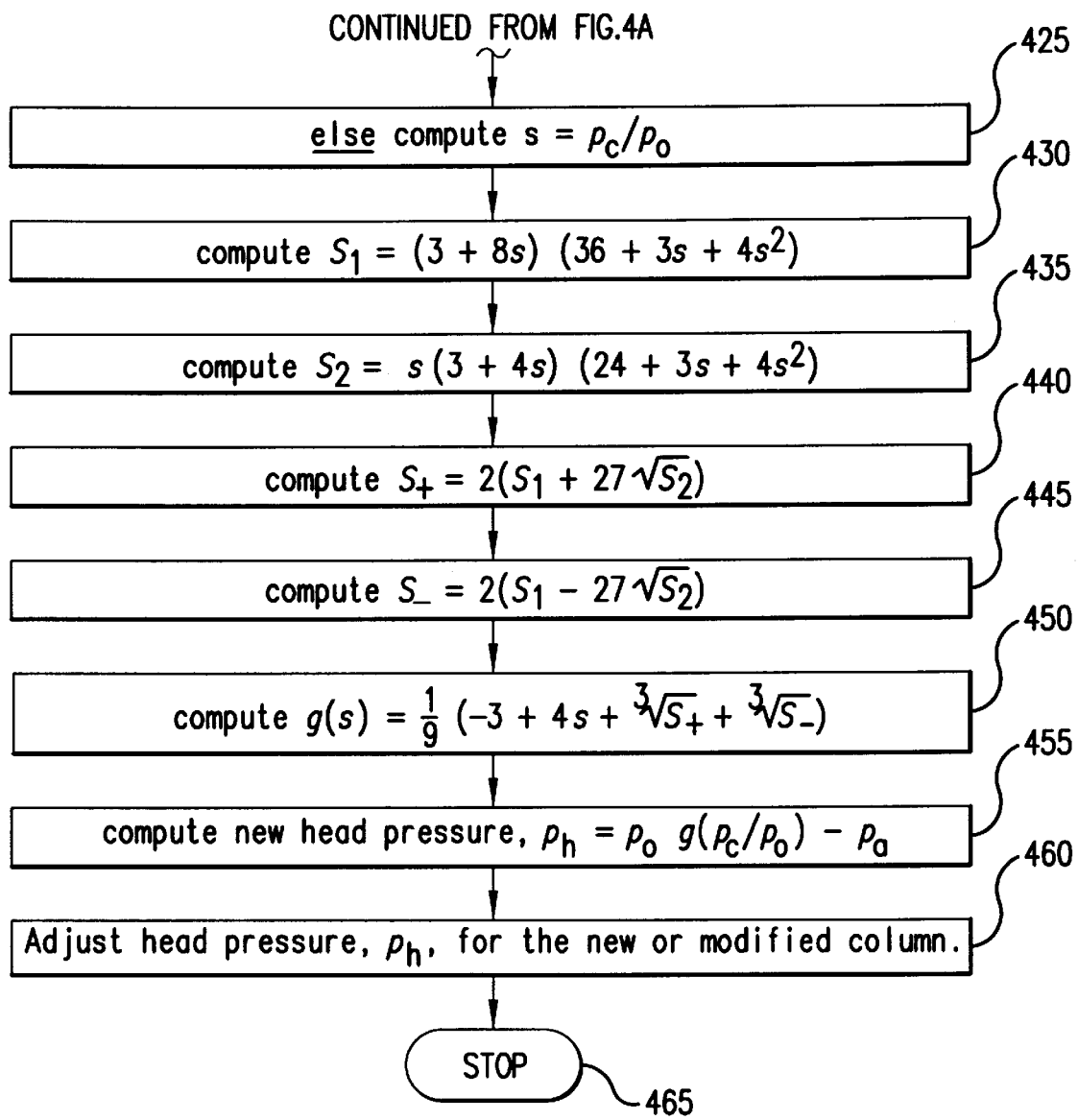

Step 400, in FIG. 4, indicates the start of the method for adjusting column head pressure. A method for calculating (step 410) and adjusting column head pressure to effect retention time locking where the column specific plate capacity, $N_{c,new}$, and film thickness, $d_{s,new}$, of the new column are supplied with the column while nominal void time, $t_{M,nom}$, and the nominal film thickness, $d_{s,nom}$, for a chromatographic method are measured and stored with other method parameters when the method was originally developed. In particular, the head pressure, $p_h$, required to lock the retention times of a new column to those of an old column can be found by first calculating the compressed pressure drop, $p_c$, as $$i \; p_c = 32(d_{s,new}/d_{s,nom})(N_{c,new})^2 \eta/t_{M,nom},$$

where $\eta$ is carrier gas viscosity, and $t_M$ by calculating the new column head pressure, $p_h$, by one of the following two ways depending on the value of outlet pressure drop, $p_o$.

(i) When $$p_o = 0 \; (\text{vacuum at the outlet}) \qquad (\text{step 415}),$$

then the new head pressure, $p_h$, can be found (step 420) as $$p_h = (4/3)p_c - p_a$$

where $p_a$ is ambient pressure.

(ii) In all other cases, the new head pressure, $p_h$, can be found (step 455) as:

$$p_h = p_o g(p_c/p_o) - p_a.$$

where, for any $s = p_c/p_o$ (step 425), the function $g(s)$ can be calculated by first computing two quantities, $S_1$ and $S_2$, for a given s, as $$S_1 = (3+8s)(36+3s+4s^2), \qquad (\text{step 430})$$

$$S_2 = s(3+4s)(24+3s+4s^2); \qquad (\text{step 435})$$

next, by using quantities $S_1$ and $S_2$ to calculate two more quantities, $S_+$ and $S_-$, as $$S_+ = 2(S_1 + 27\sqrt{S_2}), \qquad (\text{Step 400})$$

$$S_- = 2(S_1 - 27\sqrt{S_2}); \qquad (\text{Step 445})$$

and, finally, by calculating the value of $g(s)$ (step 450) as $$g(s) = \frac{1}{9}\left(-3 + 4s + \sqrt[3]{S_+} + \sqrt[3]{S_-}\right).$$

The head pressure for the new or modified column is then adjusted (step 460) based on the results of the calculation in step 455, $p_h = p_o g(p_c/p_o) - p_a$. Step 465 indicates the completion of the method for adjusting column head pressure.

2. No Known Void Time or Film Thickness

Figure 5:
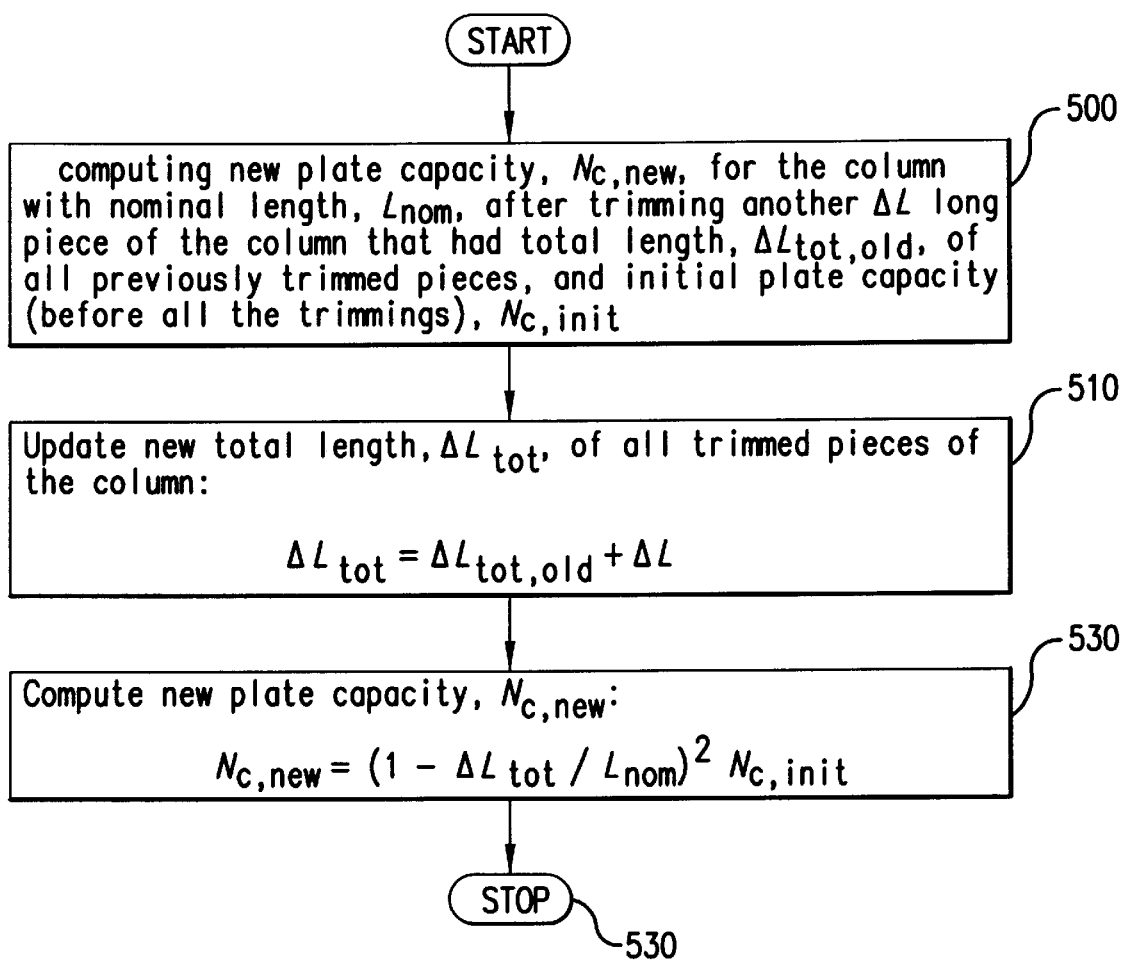
FIG. 5 illustrates method steps associated with the invention.

Step 500, in FIG. 5, indicates the start of the method for computing a new plate capacity. A flow chart of the invention's method steps where no nominal void time and film thickness for the method are known, but plate capacity, $N_{c,old}$, and film thickness, $d_{s,old}$, together with the compressed pressure drop, $p_{c,old}$, in a previously used ("old") column are known and entered (Step 510) such that the value of the compressed pressure drop, $p_c$ for the new column can be calculated (Step 520) as:

$$p_c = (d_{s,new}/d_{s,old})(N_{c,new}/N_{c,old})^2 p_{c,old}$$

The new head retention time locking head pressure, $p_h$, be calculated as for $p_o = 0$ (vacuum at the outlet) and all other cases as described in the previous section. Step 530 indicates the completion of the method for computing a new plate capacity.

c. Correction for Chance in Column Length or Plate Capacity

Routine maintenance of a GC instrument typically includes cutting off a portion of the column, reducing the column length and, as a result, reducing the plate capacity, $N_c$, of the column.

$$\Delta L_{tot} = \Delta L_1 + \Delta L_2 + \Delta L_3 +$$

head pressure adjustment to a new column head pressure, $p_h$, to effect retention time locking, can be calculated. Here, $\Delta L_1$, $\Delta L_2$, $\Delta L_3$, are individual adjustments of the column length at each maintenance. There are several ways to calculate new head pressure, $p_h$, after each adjustment, if nominal column length, $L_{nom}$, for the untrimmed column is known.

The first method is based on the knowledge of initial head pressure, $p_{h,init}$, for that column prior to all trimmings. In that case, the new retention time locking head pressure, $p_h$, after the column trimmings can be derived from its compressed equivalent, $p_c$, as previously set forth in regards to identifying plate capacity during the manufacturing of the column such that the compressed equivalent, $p_c$, of $p_h$ equals:

$$p_c = (1 - \Delta L_{tot}/L_{nom})^2 p_{c,init}$$

From this value, one can find new retention time locking value, $p_h$, of the head pressure as previously set forth before.

Alternatively, using initial value, $N_{c,init}$, of plate capacity for a new column, one can compute new value, $N_{c,new}$, of that quantity after each trimming from expression $$N_{c,new}=(1-\Delta L_{tot}/L_{nom})^2 N_{c,init}. \qquad 5$$

Experimental Data

A standard 16-component mixture of polyaromatic hydrocarbons (PAH) was analyzed using 9 (nine) 30 m×0.25 mm×0.25 μm HP-5MS columns (HP part No. 19091S-433) and helium as a carrier gas. For these tests, a method with the nominal head pressure of 25 psi and temperature program 45° C. (1 min), 18° C./min to 160° C., 10° C./min. to 325° C., 20° C./min to 350° C. (2 min) was developed. The same temperature program was used in all subsequent temperature programmed analyses.

Figure 6:
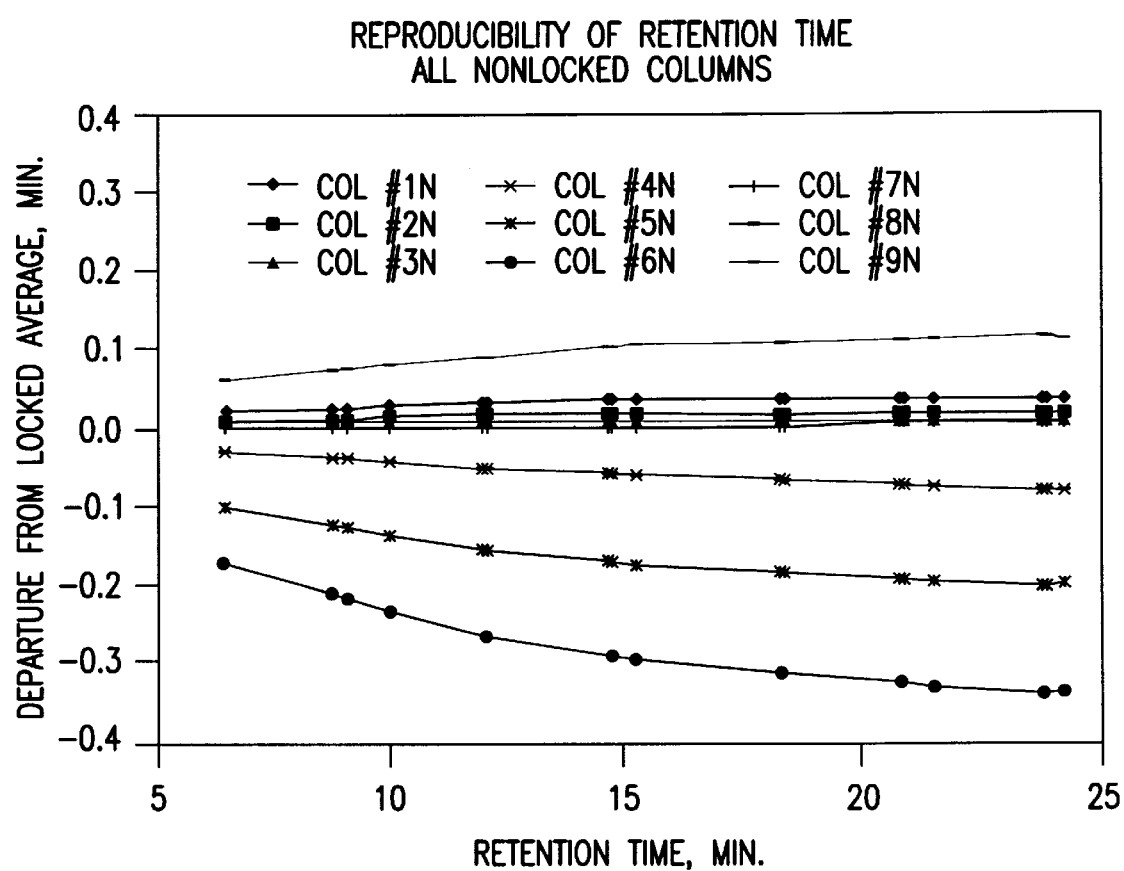
FIG. 6 illustrates actual chromatographic results (sixteen peaks) of a prior art GC that is not using the invention.

First, the temperature programmed analysis was made using each column without RTL, (25 psi head pressure was used with each column). The spread of retention times for each of 16 peaks in the mixture is shown in FIG. 6. To test the proposed retention time locking techniques, first, plate capacity, $N_c$, and film thickness, $d_s$, in each column were measured. To do so, a two-component mixture of methane and methylene chloride was analyzed with each column at isothermal temperature of 135° C. and 25 psi head pressure. From the results of these tests, the values of $N_c$ and $d_s$ were calculated for each column.

Figure 7:
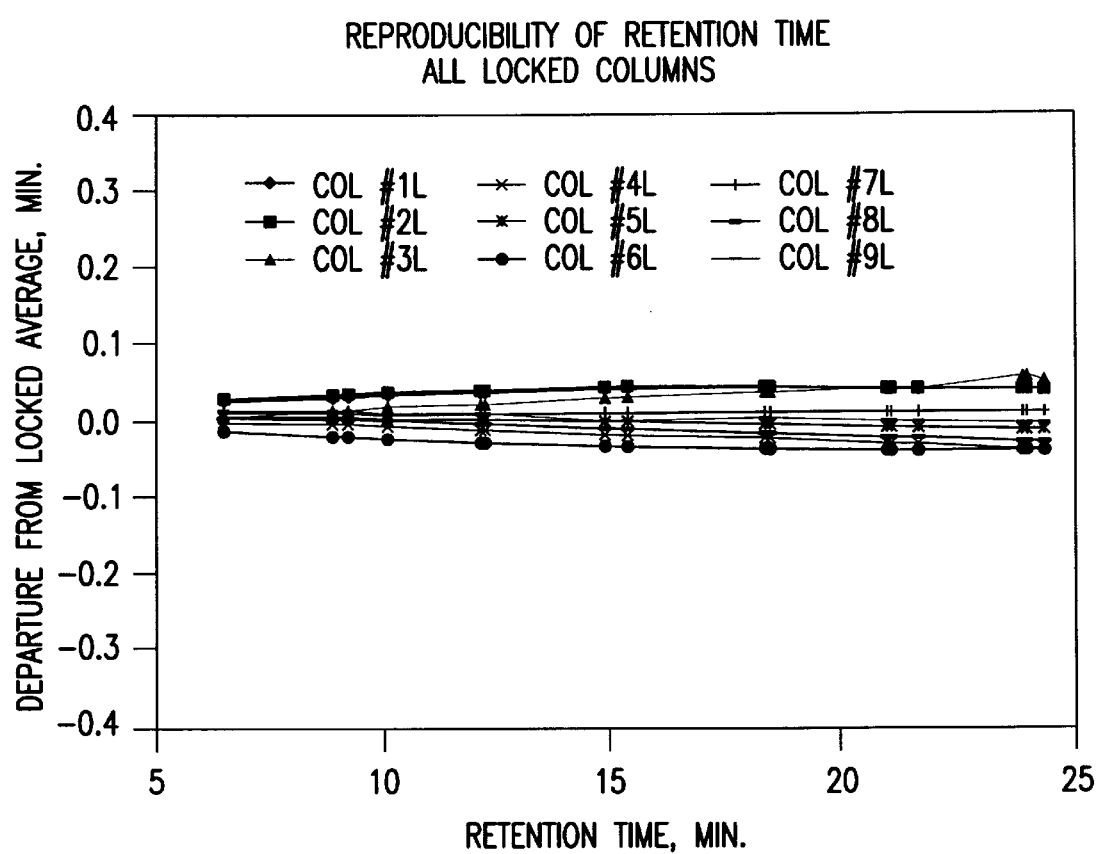
FIG. 7 illustrates actual chromatographic results (sixteen peaks) of a prior art GC that is using the invention for retention time locking based only on differences in plate capacity, $N_c$.

The column-specific values of $N_c$ and $d_s$ were used to compute individual head pressure for each column taking 25 psi as a nominal value. Two types of the temperature programmed RTL experiments were made. In one set of experiments, RTL was used only to compensate for the differences in $N_c$, (i.e. to calculate the column specific values of the head pressure, only the differences in $N_c$ were taken into account while the differences in $d_s$ were ignored). The results in FIG. 7 show about an order of magnitude reduction in column-to-column non-reproducibility of retention times has been achieved for the entire set of columns.

Figure 8:
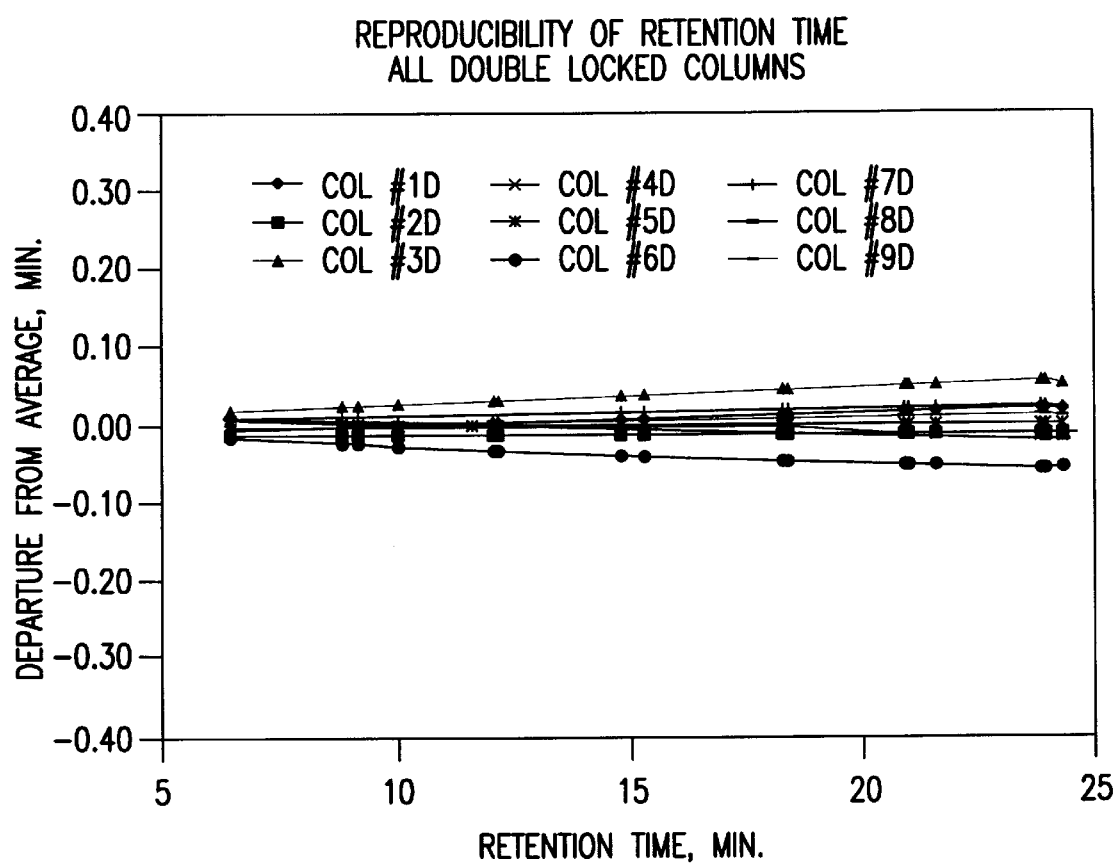
FIG. 8 illustrates actual chromatographic results (sixteen peaks) of a prior art GC that is using the invention for retention time locking of the peaks for nine separate columns based on the combination of plate capacity, $N_c$, and film thickness, $d_s$.

In another set of experiments, the differences in both $N_c$ and $d_s$ were taken into account and provide for further reduction in column-to-column non-reproducibility of retention times for some columns (FIG. 8).

While the invention has been described and illustrated with reference to specific embodiments in the area of the column specific parameters of plate capacity and film thickness, those skilled in the art will recognize that modification and variations may be made such that the invention is equally applicable to derivatives and combinations of these parameters, as well as the manual or automated implementation of retention time locking based on these parameters.

What is claimed is:

1. A method for adjusting the column head pressure of a GC instrument such that the retention times of analytes eluting from a new or shortened column installed on the GC instrument are matched to those of similar analytes eluting from the existing column having the same type of stationary phase, and phase ratio, but where the new and existing columns have different dimensions, different carrier gas types and optionally different outlet pressure, comprising the method steps of:

calculating a new column head pressure, $p_h$, in accordance with the following equation:

$$p_h = p_o g(p_c/p_o) - p_a,$$

where, $p_h$=column head pressure, $p_o$=column outlet pressure, $p_a$=ambient pressure, $p_c$=compressed pressure drop, defined as $p_c = r \cdot \bar{u}$, where, $\bar{u}$ is average velocity of carrier gas and r, pneumatic resistance of the column calculated for the columns with circular cross-section as:

$$r = \frac{32\eta L}{d_c^2},$$

where, $d_c$=column internal diameters

L=column length,

η=carrier gas viscosity, and where for any $s=p_c/p_o$, function g(s) can be calculated as follows:

$$g(s) = \frac{1}{9}\left(-3 + 4s + \sqrt[3]{s_+} + \sqrt[3]{s_-}\right),$$

where, $$s_+ = 2\left(s_1 + 27\sqrt{s_2}\right)$$

$$s_- = 2\left(s_1 - 27\sqrt{s_2}\right)$$

where, $s_1$ and $s_2$, are calculated as:

$$s_1=(3+8s)(36+3s+4s^2),$$

$$s_2=s(3+4s)(24+3s+4s^2);$$

adjusting the column head pressure of the GC instrument to the new column head pressure, whereby the retention times of analytes eluting from the new column are the same as through the existing column.

2. The method for adjusting the column head pressure of a GC instrument as claimed in claim 1, wherein the plate capacity, $N_{c,old}$, film thickness, $d_{s,old}$, and the compressed pressure drop, $p_{c,old}$, of the previously used column are known, and wherein the compressed pressure drop, $p_c$, for the new column with plate capacity, $N_{c,new}$, and film thickness, $d_{s,new}$, is determined according to the following:

$$p_c=(d_{s,new}/d_{s,old})(N_{c,new}/N_{c,old})^2 p_{c,old}$$

where:

$d_s$=stationary phase film thickness $N_c$=plate capacity of the column, defined as $$N_c=L/d_c.$$

3. The method for adjusting the column head pressure of a GC instrument as claimed in claim 1, wherein the nominal void time, $t_{M,nom}$, and the nominal film thickness, $d_{s,nom}$, for the method are known, and wherein the compressed pressure drop, $p_c$, for the new column with plate capacity, $N_{c,new}$, and film thickness, $d_{s,new}$, is determined according to the following:

$$p_c=32(d_{s,new}/d_{s,nom})(N_{c,new})^2\eta/t_{M,nom}$$

where:

$\eta$=viscosity of carrier gas.

4. The method for calculating and adjusting the column head pressure of a GC instrument as claimed in claim 1, further comprising the method steps of:

manufacturing a column with a known type of stationary phase film, known nominal film thickness, $d_{s,nom}$, and known nominal retention factor, $k_{nom}$, for a known analyte;

measuring under isothermal conditions, void time, $t_M$, and retention time $t_R$, of a known analyte in the manufactured column;

calculating retention factor, k, of a known analyte in the manufactured column as $$k = \frac{t_r}{t_M - 1};$$

calculating stationary phase film thickness, $d_s$, in the manufactured column as $$d_s = \left(\frac{k}{k_{nom}}\right) d_{s,nom};$$

providing the calculated film thickness, $d_s$, with the column;

calculating compressed pressure drop, $p_s$, when the column is installed in a GC instrument;

calculating head pressure, $p_h$; and adjusting head pressure to the calculated value.

5. The method for calculating and adjusting the column head pressure of a GC instrument as claimed in claim 4, wherein the plate capacity, $N_{c,old}$, film thickness, $d_{s,old}$, and the compressed pressure drop, $p_{c,old}$, of the previously used column are known, and wherein the compressed pressure drop, $p_c$, for the new column with plate capacity, $N_{c,new}$, and film thickness, $d_{s,new}$, is determined according to the following:

$$p_c=(d_{s,new}/d_{s,old})(N_{c,new}/N_{c,old})^2 p_{c,old}$$

where:

$d_s$=stationary phase film thickness $N_c$=plate capacity of the column, defined as i $N_c=L/d_c$.

6. The method for calculating and adjusting the column head pressure of a GC instrument as claimed in claim 4, wherein the nominal void time, $t_{M,nom}$, and the nominal film thickness, $d_{s,nom}$, for the method are known, and wherein the compressed pressure drop, $p_c$, for the new column with plate capacity, $N_{c,new}$, and film thickness, $d_{s,new}$, is determined according to the following:

$$p_c=32(d_{s,new}/d_{s,nom})(N_{c,new})^2\eta/t_{M,nom}$$

where:

$\eta$=viscosity of carrier gas.

7. The method for calculating and adjusting the column head pressure of a GC instrument as claimed in claim 4, the step of calculating a new column head pressure, $p_h$, is in accordance with the following equation:

$$p_h=p_o g(p_c/p_o)-p_a$$

where, $p_h$=column head pressure, $p_o$=column outlet pressure, $p_a$=ambient pressure, $p_c$=compressed pressure drop, defined as $p_c=r\cdot\bar{u}$ where $\bar{u}$ is average velocity of carrier gas and r—pneumatic resistance of the column calculated for the columns with circular cross-section as $$r = \frac{32\eta L}{d_c^2}$$

where $d_c$=column internal diameter

L=column length $\eta$=carrier gas viscosity and where for any $s=p_c/p_o$, function g(s) can be calculated as follows:

$$g(s) = \frac{1}{9}\left(-3 + 4s + \sqrt[3]{S_+} + \sqrt[3]{S_-}\right)$$

where $$S_+ = 2\left(S_1 + 27\sqrt{S_2}\right)$$
$$S_- = 2\left(S_1 - 27\sqrt{S_2}\right)$$

where, $S_1$ and $S_2$, are calculated as $$S_1=(3+8s)(36+3s+4s^2),$$

$$S_2=s(3+4s)(24+3s+4s^2).$$

8. The method for calculating and adjusting the column head pressure of a GC instrument as claimed in claim 7, wherein the nominal void time, $t_{M,nom}$, and the nominal film thickness, $d_{s,nom}$, for the method are known, and wherein the compressed pressure drop, $p_c$, for the new column with plate capacity, $N_{c,new}$, and film thickness, $d_{s,new}$, is determined according to the following:

$$p_c=32(d_{s,new}/d_{s,nom})(N_{c,new})^2\eta/t_{M,nom}$$

where:

$\eta$=viscosity of carrier gas.

9. The method for calculating and adjusting the column head pressure of a GC instrument as claimed in claim 1, wherein the step of calculating new plate capacity, $N_{c,new}$, after trimming the column with known initial plate capacity, $N_{c,init}$, and known initial nominal column length, $L_{nom}$, comprises the method steps of:

recording the length of the trimmed piece, $\Delta L_1$, $\Delta L_2$, $\Delta L_3$, . . . , of the column at each act of trimming;

calculating the total length, $\Delta L_{tot}$, of the trimmed pieces of the column as $$\Delta L_{tot}=\Delta L_1+\Delta L_2+\Delta L_3+\ldots;$$

calculating new plate capacity, Nc,new, of the trimmed column as $$N_{c,new} = \left(\frac{1 - \Delta L_{tot}}{L_{nom}}\right)^2 N_{c,init};$$

calculating compressed pressure drop;

calculating head pressure, ph, of the trimmed column; and adjusting head pressure to the calculated value.

10. The method for calculating and adjusting the column head pressure of a GC instrument as claimed in claim 9, wherein the plate capacity, $N_{c,old}$, film thickness, $d_{s,old}$, and the compressed pressure drop, $p_{c,old}$, of the previously used column are known, and wherein the compressed pressure drop, $p_c$, for the new column with plate capacity, $N_{c,new}$, and film thickness, $d_{s,new}$, is determined according to the following:

$$p_c = (d_{s,new}/d_{s,old})(N_{c,new}/N_{c,old})^2 p_{c,old}$$

where:

$d_s$ = stationary phase film thickness $N_c$ = plate capacity of the column, defined as $$N_c = L/d_c.$$

11. A method for adjusting the column head pressure of a GC instrument such that the retention times of analytes eluting from a new or shortened column installed on the GC instrument are matched to those of similar analytes eluting from an existing column having the same type of stationary phase, but where the new and existing columns have different dimensions, different carrier gas types and optionally different outlet pressure, comprising the method steps of:

manufacturing a column;

measuring void time, $t_M$, in the manufactured column;

calculating compressed pressure drop, $p_c$, for the conditions of the void time measurement as:

$$p_c = \frac{3}{4} \cdot \frac{(p_h + p_a - p_o)(p_h + p_a + p_o)^2}{p_o(p_h + p_a + p_o)(p_h + p_a)^2}$$

in a general case, or as:

$$p_c = \frac{3}{4} \cdot \frac{p_h(2p_a + p_h)^2}{3p_a^2 + 3p_a p_h + p_h^2}$$

when $p_o = p_a$ (outlet pressure is the same as ambient pressure), or as:

$$p_c = \frac{3}{4}(p_h + p_a)$$

when $p_o = 0$ (outlet at vacuum);

calculating plate capacity, $N_c$, of the manufactured column as:

$$N_c = \sqrt{\frac{p_c t_M}{32\eta}};$$

providing the calculated plate capacity, $N_c$, with the column;

calculating compressed pressure drop, $p_c$, when the column is installed in the GC instrument;

calculating head pressure, $p_h$;

adjusting head pressure to the calculated value.

12. The method for calculating and adjusting the column head pressure of a GC instrument as claimed in claim 11, wherein the plate capacity, $N_{c,old}$, film thickness, $d_{s,old}$, and the compressed pressure drop, $p_{c,old}$, of the previously used column are known, and wherein the compressed pressure drop, $p_c$, for the new column with plate capacity, $N_{c,new}$, and film thickness, $d_{s,new}$, is determined according to the following:

$$p_c = (d_{s,new}/d_{s,old})(N_{c,new}/N_{c,old})^2 p_{c,old}$$

where:

$d_s$ = stationary phase film thickness $N_c$ = plate capacity of the column, defined as $$N_c = L/d_c.$$

13. The method for calculating and adjusting the column head pressure of a GC instrument as claimed in claim 11, wherein the nominal void time, $t_{M,nom}$, and the nominal film thickness, $d_{s,nom}$, for the method are known, and wherein the compressed pressure drop, $p_c$, for the new column with plate capacity, $N_{c,new}$, and film thickness, $d_{s,new}$, is determined according to the following:

$$p_c = 32(d_{s,new}/d_{s,nom})(N_{c,new})^2 \eta/t_{M,nom}$$

where:

$\eta$ = viscosity of carrier gas.

14. The method for calculating and adjusting the column head pressure of a GC instrument as claimed in claim 11, the step of calculating a new column head pressure, $p_h$, is in accordance with the following equation:

$$p_h = p_o g(p_c/p_o) - p_a$$

where, $p_h$ = column head pressure, $p_o$ = column outlet pressure, $p_a$ = ambient pressure, $p_c$ = compressed pressure drop, defined as $p_c = r \cdot \bar{u}$ where $\bar{u}$ is average velocity of carrier gas and r—pneumatic resistance of the column calculated for the columns with circular cross-section as $$r = \frac{32\eta L}{d_c^2}$$

where $d_c$ = column internal diameter

L = column length $\eta$ = carrier gas viscosity and where for any $s = p_c/p_o$, function $g(s)$ can be calculated as follows:

$$g(s) = \frac{1}{9}\left(-3 + 4s + \sqrt[3]{S_+} + \sqrt[3]{S_-}\right)$$

where $$S_+ = 2(S_1 + 27\sqrt{S_2})$$
$$S_- = 2(S_1 - 27\sqrt{S_2})$$

where, $S_1$ and $S_2$, are calculated as $$S_1 = (3+8s)(36+3s+4s^2),$$
$$S_2 = s(3+4s)(24+3s+4s^2);$$

adjusting the column head pressure of the GC to the new column head pressure, whereby the retention times of analytes eluting from the new column are the same as through the existing column.

15. A method for adjusting the column head pressure of a GC instrument such that the retention times of analytes eluting from a new or shortened column installed on the GC instrument are matched to those of similar analytes eluting from the existing column having the same type of stationary phase, and phase ratio, but where the new and existing columns have different dimensions, different carrier gas types and optionally different outlet pressure, comprising:
calculating a new column head pressure; and
adjusting the column head pressure of the GC instrument to the new column head pressure, whereby the retention times of analytes eluting from the new column are the same as through the existing column.

16. The method of claim 15, wherein the plate capacity, film thickness, and the compressed pressure drop, of the previously used column are known, and wherein the compressed pressure drop for the new column is calculated by:
determining the ratio of change in stationary film thickness;
determining the ratio of change in plate capacity; and
multiplying the ratio of change in stationary film thickness with the square of the ratio of change in plate capacity and the compressed pressure drop of the previously used column.

17. The method of claim 15, wherein the nominal void time and the nominal film thickness are known, and wherein the compressed pressure drop for the new column is calculated by:
determining the viscosity of the gas;
determining the ratio of change in stationary film thickness;
squaring the new plate capacity;
multiplying a predefined number by the ratio of change in stationary film thickness with the square of the new plate capacity and the viscosity of the gas to create a numerator; and
dividing the numerator by the nominal void time.

18. A method for calculating and adjusting the column head pressure of a GC instrument such that the retention times of analytes eluting from a new or shortened column installed on the GC instrument are matched to those of similar analytes eluting from an existing column having the same type of stationary phase, but where the new and existing columns have different dimensions, different carrier gas types and optionally different outlet pressure, comprising:
manufacturing a column;
measuring void time in the manufactured column;
calculating compressed pressure drop for the conditions of the void time;
calculating plate capacity of the manufactured column;
providing the calculated plate capacity with the column;
calculating compressed pressure drop when the column is installed in the GC instrument;
calculating head pressure; and
adjusting head pressure to the calculated value.

19. The method of claim 18, wherein the plate capacity, film thickness, and the compressed pressure drop of the previously used column are known, and wherein the compressed pressure drop for the new column is determined by:
determining the ratio of change in stationary film thickness;
determining the ratio of change in plate capacity; and
multiplying the ratio of change in stationary film thickness with the square of the ratio of change in plate capacity and the compressed pressure drop of the previously used column.

20. The method of claim 18, wherein the nominal void time and the nominal film thickness are known, and wherein the compressed pressure drop for the new column is calculated by:
determining the viscosity of the gas;
determining the ratio of change in stationary film thickness;
squaring the new plate capacity;
multiplying a predefined number by the ratio of change in stationary film thickness with the square of the new plate capacity and the viscosity of the gas to create a numerator; and
dividing the numerator by the nominal void time.

21. The method of claim 18, wherein the step of calculating a new column head pressure comprises:
measuring column outlet pressure;
measuring ambient pressure;
calculating the compressed pressure drop;
calculating the result of a function of the ratio of compressed pressure drop to the outlet pressure; and
subtracting the ambient pressure from the product of outlet pressure and the function of the ratio of compressed pressure drop to outlet pressure.

22. The method of claim 18, wherein the method further comprises:
manufacturing a column with a known type of stationary phase film, known nominal film thickness and known nominal retention factor for a known analyte;
measuring under isothermal conditions, void time and retention time of a known analyte in the manufactured column;
calculating the retention factor of a known analyte in the manufactured column;
calculating stationary phase film thickness in the manufactured column;
providing the calculated film thickness with the column;
calculating compressed pressure drop when the column is installed in a new GC instrument;
calculating head pressure; and
adjusting head pressure to the calculated value.

23. The method of claim 22, wherein the plate capacity, film thickness, and the compressed pressure drop of the previously used column are known, and wherein the compressed pressure drop for the new column is calculated by:
- determining the ratio of change in stationary film thickness;
- determining the ratio of change in plate capacity; and
- multiplying the ratio of change in stationary film thickness with the square of the ratio of change in plate capacity and the compressed pressure drop of the previously used column.

24. The method of claim 22, wherein the nominal void time and the nominal film thickness are known and wherein the compressed pressure drop for the new column is calculated by:
- determining the viscosity of the gas;
- determining the ratio of change in stationary film thickness;
- squaring the new plate capacity;
- multiplying a predefined number by the ratio of change in stationary film thickness with the square of the new plate capacity and the viscosity of the gas to create a numerator; and
- dividing the numerator by the nominal void time.

25. The method of claim 22, wherein the step of calculating a new column head pressure comprises:
- measuring column outlet pressure;
- measuring ambient pressure;
- calculating the compressed pressure drop;
- calculating the result of a function of the ratio of compressed pressure drop to the outlet pressure; and
- subtracting the ambient pressure from the product of outlet pressure and the function of the ratio of compressed pressure drop to outlet pressure.

26. The method of claim 25, wherein the step of calculating the compressed pressure drop comprises:
- determining the viscosity of the gas;
- determining the ratio of change in stationary film thickness;
- squaring the new plate capacity;
- multiplying a predefined number by the ratio of change in stationary film thickness with the square of the new plate capacity and the viscosity of the gas to create a numerator; and
- dividing the numerator by the nominal void time.

27. The method of claim 22, wherein the step of calculating the new plate capacity comprises:
- recording the length of the trimmed piece of the column at each act of trimming;
- calculating the total length of the trimmed pieces of the column;
- calculating the new plate capacity of the trimmed column;
- calculating compressed pressure drop;
- calculating head pressure of the trimmed column; and
- adjusting head pressure to the calculated value.

28. The method of claim 27, wherein the plate capacity, film thickness, and the compressed pressure drop of the previously used column are known, and wherein the compressed pressure drop for the new column is calculated by:
- determining the ratio of change in stationary film thickness;
- determining the ratio of change in plate capacity; and
- multiplying the ratio of change in stationary film thickness with the square of the ratio of change in plate capacity and the compressed pressure drop of the previously used column.

\* \* \* \* \*